United States Patent
Lee et al.

(10) Patent No.: US 8,281,672 B2
(45) Date of Patent: Oct. 9, 2012

(54) AUTOMATABLE ASEPTIC SAMPLE WITHDRAWAL SYSTEM

(75) Inventors: Chanyong Brian Lee, Camarillo, CA (US); Daniel Giroux, Cardiff by the Sea, CA (US)

(73) Assignee: PBS Biotech, Inc., Camarillo, CA (US)

( * ) Notice: Subject to any disclaimer, the term of this patent is extended or adjusted under 35 U.S.C. 154(b) by 389 days.

(21) Appl. No.: 12/727,719

(22) Filed: Mar. 19, 2010

(65) Prior Publication Data

US 2010/0236340 A1  Sep. 23, 2010

Related U.S. Application Data

(60) Provisional application No. 61/161,831, filed on Mar. 20, 2009.

(51) Int. Cl.
*G01N 1/00* (2006.01)
(52) U.S. Cl. ........................................... 73/863
(58) Field of Classification Search .............. 73/863
See application file for complete search history.

(56) References Cited

U.S. PATENT DOCUMENTS

| | | | |
|---|---|---|---|
| 4,101,384 A | 7/1978 | Faust et al. | |
| 4,942,770 A | 7/1990 | Seifert et al. | |
| 4,956,082 A | 9/1990 | Choi | |
| 5,081,035 A | 1/1992 | Halberstadt et al. | |
| 7,628,528 B2 | 12/2009 | Zeikus | |
| 2002/0110915 A1 | 8/2002 | Shaaltiel | |
| 2003/0230521 A1 | 12/2003 | Schick | |
| 2004/0259241 A1* | 12/2004 | Barringer, Jr. | 435/309.2 |
| 2005/0158851 A1 | 7/2005 | Furey | |
| 2005/0272146 A1 | 12/2005 | Hodge et al. | |
| 2007/0072285 A1* | 3/2007 | Barringer, Jr. | 435/286.5 |
| 2007/0128087 A1* | 6/2007 | Cannizzaro et al. | 422/119 |
| 2007/0271997 A1* | 11/2007 | O'Brien | 73/23.37 |

(Continued)

FOREIGN PATENT DOCUMENTS
DE  3935050 C1  4/1991
(Continued)

OTHER PUBLICATIONS

International Search Report and Written Opinion for PCT/US2010/027964, 14 pgs. (mailed Sep. 20, 2010).

*Primary Examiner* — Hezron E Williams
*Assistant Examiner* — Rodney T Frank
(74) *Attorney, Agent, or Firm* — Rothwell, Figg, Ernst & Manbeck, P.C.

(57) ABSTRACT

An aseptic sampling system includes substantially sealed sampling lines connecting one or more sample container to a vessel containing the fluid to be sampled. A flow control system includes valves and/or clamps placed strategically along the sampling lines and filtered vent lines are provided at strategic locations relative to a reversible fluid pump in communication with the sampling lines. The clamps are selectively actuated, the vent lines are selectively opened or closed, and the pump is operated in a forward or reverse direction to permit a volume of sample fluid to be drawn from the vessel and into a sample container and to permit fluid to be purged from the sampling lines either into the sample container or back into the vessel. Thus, sampling and purging can be accomplished without opening the system to potentially contaminating agents and without wasting or having to properly dispose the fluid.

14 Claims, 6 Drawing Sheets

U.S. PATENT DOCUMENTS

| | | |
|---|---|---|
| 2008/0022786 A1* | 1/2008 | Sann et al. ............... 73/863.86 |
| 2008/0060459 A1* | 3/2008 | Rich ........................ 73/864.34 |
| 2008/0261299 A1 | 10/2008 | Zeikus et al. |
| 2008/0268530 A1 | 10/2008 | Zeikus et al. |
| 2008/0308494 A1 | 12/2008 | Barringer et al. |
| 2009/0269849 A1 | 10/2009 | Lee et al. |
| 2010/0018329 A1* | 1/2010 | Grziwotz et al. ......... 73/863.02 |
| 2010/0043883 A1* | 2/2010 | Yu et al. ........................ 137/1 |
| 2010/0047122 A1 | 2/2010 | Barringer et al. |

FOREIGN PATENT DOCUMENTS

| | | |
|---|---|---|
| EP | 1508791 A1 | 2/2005 |
| WO | WO 2008-108792 A2 | 9/2008 |
| WO | WO 2008-108792 A3 | 9/2008 |

* cited by examiner

AUTOMATABLE ASEPTIC SAMPLE WITHDRAWAL SYSTEM

PRIORITY CLAIM

This application claims the benefit under 35 U.S.C. 119(e) of U.S. Provisional Application No. 61/161,831, filed Mar. 20, 2009, the disclosure of which is hereby incorporated by reference in its entirety.

FIELD OF THE INVENTION

The invention relates to mammalian cell culture or microbial fermentation and, more particularly, to systems and methods for aseptically withdrawing discrete samples of culture material from a vessel containing such material.

BACKGROUND

Cell culture (mammalian cell culture) procedures using a bioreactor or fermentation (microbial cell culture) procedures using a fermentor or fermentation vessel embody techniques for growing and proliferating unit cells separate from an organism and is widely used in biology, medical science, pharmacy, and agriculture. Additionally, the use of biological cultivation procedures has expanded into other disciplines, such as the treatment of waste water or oil.

Apparatuses designed for cultivation of microbial organisms or eukaryotic cells, known as bioreactors or fermentors, have been used for production of various biological or chemical products in the pharmaceutical, biotechnological and beverage industry. A typical bioreactor includes a vessel for containing culture medium in a sterile environment that provides the various nutrients required to support growth of the homogeneous biological agents of interest.

Effective cell culture process requires appropriate supplies of nutrient substances, such as glutamine, glucose, and other medium components, and gas, such as oxygen and carbon dioxide, for the growing cells in a bioreactor. In addition, timely control of physiological conditions, such as appropriate pH, temperature, and osmolarity is required for mass cell culture production. In order to provide optimal culture conditions in a bioreactor, rapid and effective mixing in the culture medium is prerequisite, and cells should be uniformly dispersed throughout the culture medium without aggregation in any portion of the cultivation vessel.

During a cell culture process, aseptic withdrawal of a culture broth sample that is representative of the overall cell culture condition is critical for monitoring the performance of the cell culture or fermentation process and for troubleshooting any process problems. The aseptic sampling step is also applicable in medium batching and holding vessels, for which maintaining the desired dissolved carbon dioxide level can be critical to ensuring the proper pH of the cell culture medium. Conventional sample withdrawal from a bioreactor, fermentor, or medium holding vessel, however, is typically performed by a series of manual operations, including purging the sampling line, connecting a sample device aseptically to the line, removing the sample from the bioreactor, and closing the line. The purge step is usually required at the beginning of each sampling step to flush the residual sample in the sampling line from the previous sampling into a waste reservoir. The conventional sample withdrawal procedure results in waste of sample held up in the main sampling line and requires an additional step to switch the sampling line between the waste reservoir and the actual sample container. The conventional sampling procedure also creates the additional step of properly disposing the flushed material.

SUMMARY

Aspects of the invention are embodied in a system for withdrawing discrete fluid samples from a vessel. The system includes a main sampling line in fluid communication with the vessel, a pump in fluid communication with the main sampling line and adapted to selectively pump fluid from in the main sampling line in a first direction away from the vessel or a second direction toward the vessel, a first vent port in fluid communication with the main sampling line and disposed on a first side of the pump, a second vent port in fluid communication with the main sampling line and disposed on a second side of the pump, one or more sample containers in fluid communication with a portion of the main sampling line on the second side of the pump, and a flow control system adapted to be selectively configured to open or close each of the first and second vent ports, open or close one or more portions of the main sampling line, and open or close each sample container. When the flow control system is in a first configuration, the first and second vent ports are closed, the main sampling line is open on the first and second sides of the pump, and at least one sample container is open, so that the pump can be operated in a first direction to move an amount of fluid from the vessel, through a portion of the main sampling line, and into the open sample container. When the flow control system is in a second configuration, the first vent port is closed, the second vent port is open, each of the one or more sample containers is closed, and a portion of the main sampling line on the first side of the pump is open so that the pump can be operated in a second direction to move fluid disposed in the main sampling line into the vessel without withdrawing fluid from the at least one sample container. When the flow control system is in a third configuration, the first vent port is open, the second vent port is closed, the main sampling line is closed on the first side of the pump and opened on the second side of the pump, and the at least one sample container is open so that the pump can be operated in the first direction to move fluid disposed in the main sampling line and into the open sample container without withdrawing additional fluid from the main sample container.

Other aspects of the invention are embodied in a method for aseptically removing a sample portion of a fluid from a vessel containing the fluid. A fluid flow connection is provided between the vessel and a sample container, and fluid is pumped in a first direction from the vessel to the sample container through the fluid flow connection. The vessel is then disconnected from the fluid flow connection, a vent is opened upstream from the pump, and fluid is pumped in the first direction through the fluid flow connection into the sample container without pumping any additional fluid from the vessel. The upstream vent is then closed, the vessel is reconnected to the fluid flow connection, the sample container is disconnected from the fluid flow connection, a vent is opened downstream from the pump, and fluid is pumped in a second direction opposite the first direction through the fluid flow connection and into the vessel without pumping any fluid from the sample container.

These and other features, aspects, and advantages of the present invention will become apparent to those skilled in the art after considering the following detailed description, appended claims and accompanying drawings.

DETAILED DESCRIPTION

As used herein, unless noted otherwise, the words "a" and "an" mean "one or more." Furthermore, unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

Figure 1:
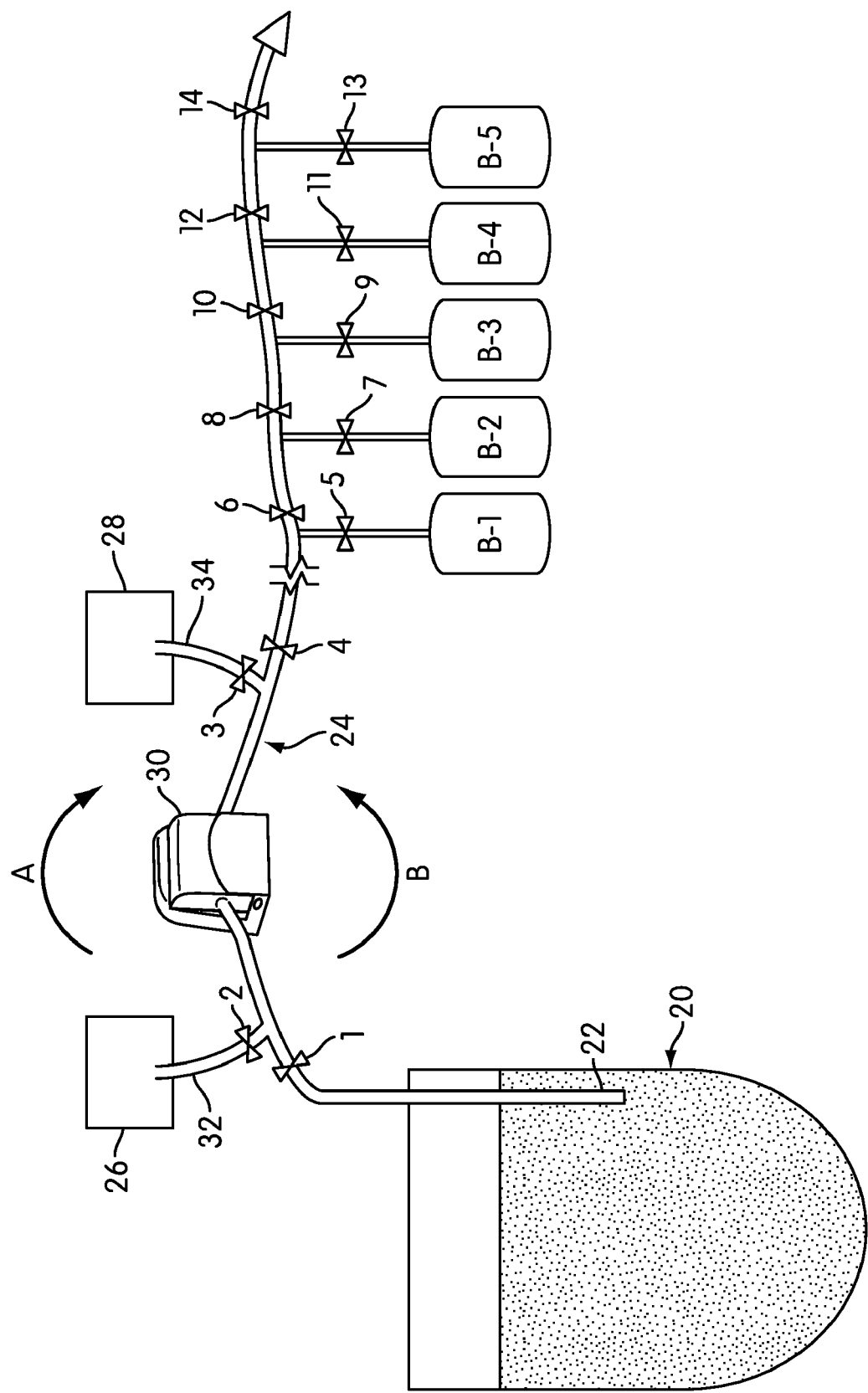
FIG. 1 is a schematic drawing of an aseptic sample withdrawal system embodying aspects of the invention.

An aseptic withdrawal system embodying aspects of the invention is shown in FIG. 1. The system includes a vessel 20, a dip tube 22 extending into the vessel 20, a sampling line 24, a bi-directional pump 30 placed in line with the sampling line 24, vent lines 32, 34 branching from the sampling line 24, filters 26, 28 disposed on the vent lines 32, 34, respectively, a flow control system which, in the illustrated embodiment, comprises a plurality of valves 1-14, and sample containers B-1-B-5 each connected to a respective secondary line branching from the main sampling line 24. Vessel 20 may be the fluid holding container of a bioreactor for mammalian cell culture, a fermentor or fermentation vessel for microbial cell culture, or fermentation, or a medium batching/holding vessel. A bioreactor with which the aseptic withdrawal system may be incorporated is described by Lee, "Bioreactor Apparatus," U.S. Patent Publication No. 2009-0269849, the disclosure of which is hereby incorporated by reference. A "medium batching/holding vessel" refers to a tank designated for either batching or holding cell culture medium at a set temperature, pressure, and agitation prior to transfer into a bioreactor or a fermentor. Such batching vessels are used in many biotech facilities to shorten the manufacturing run time, by allowing medium to be batched and held for a few days, up to a week, while a previous batch is still running in the bioreactor or fermentor. Medium batching is typically a non-sterile process, and batched medium is transferred through a sterilizing-grade filter into a medium holding tank, where it is then held under sterile conditions. Samples are typically taken during medium batching to ensure the medium has the desired pH and dissolved $CO_2$ level and may be taken after medium hold to ensure it was held as expected.

Vessel 20 may comprise a bag formed from a suitable plastic film operatively supported by a rigid frame or housing. Valves 1-14 may comprise control pinch valves, but any suitable valve can be used. For example, since valves 1-14 are simply used for automating the opening and closing of tubing, they may be replaced with any number and/or combination of clamps, hemostats, or stopcocks for manually pinching off tubing.

Pinch valves, if used, by be electronically actuated or pneumatically actuated. Suitable pinch valves are available from BioChem Fluidics Part No. 100P-2-NC-24-05 S Q. A suitable pump is the Watson Marlow 114 pump No. 010.5E20.00A. Exemplary volumes for sample containers B-1-B-5 are up to 50 mL for R&D applications and up to 1.0 L for cGMP (current good manufacturing practice) applications.

The sampling system includes the main sampling line 24 with two vent lines 32, 34 that split off from the main sampling line 24 on opposite sides of the pump 30. Each vent line 32, 34 has a vent filter 26, 28, respectively (preferably a sterilizing grade gas filter with, e.g., a 0.2 µm membrane) on its distal end. Filter 26 will be referred to as the "vessel side filter," and filter 28 will be referred to as the "sample side filter." Similarly, vent line 32 may be referred to as the "vessel side vent line," and vent line 34 will be referred to as the "sample side vent line." With the exception of the vent lines 32, 34, which are open to ambient conditions through filters 26 and 28, respectively, vessel 20, the main sampling line 24, the secondary sampling lines, and the sample containers B-1 through B-5 are preferably closed to ambient conditions (although a filtered gas exhaust may be provided in the vessel), thereby maintaining an aseptic fluid transfer path between the vessel 20 and the sample containers.

One end of the sampling line 24 is connected to the dip tube 22 that extends into the vessel 20, and the other end of the sampling line 24 is connected to a series of sample containers (e.g., bags) B-1-B-5 attached to the sampling line 24 via secondary sampling lines branching from the main sampling line 24. If the vessel 20 comprises a plastic bag, the dip tube 22 may be inserted into the vessel 20 through a port disc (not shown) heat-sealed to the bag film. If vessel 20 is made out of rigid plastic material, the dip tube 22 may also be inserted into the vessel 20 through plastic port that is molded as part of the top plate of the vessel. In an alternative embodiment, shown in FIG. 2, the end 22' of the sampling line 24 may be connected to the bottom of the vessel 20, for example, through a port disc 36 heat-sealed to the bag film. If vessel 20 is made out of rigid plastic material, the end 22' of the sampling line 24 may also be introduced to the bottom of the vessel 20 as a molded plastic channel that runs vertically on the inside of the vessel 20 from the top plate of the vessel. The number of sample containers is customizable and can be specified ahead of time, but more vessels can be added aseptically by the user through sterile tube welding. To ensure that the sampling system is sterile, i.e., free of live bacteria, other microorganisms, or bioactive DNA, the entire sampling system can be either pre-assembled and pre-sterilized (e.g., by gamma irradiation) with the vessel 20 or sterilized separately and attached to the existing sampling line through sterile tube welding or through aseptic connection devices. Sterilization may also be performed by autoclaving if the sampling system consists of material that can withstand a typical autoclave cycle.

The portion of the sampling line 24 between the two filtered lines 32, 34 is fitted to a bi-directional pump 30 (e.g., a peristaltic pump) to help drive the fluid either into one of the sample containers B-1-B-5 or back into the vessel 20, depending on the open/closed position of the valves 1-14 and the rotational direction of the pump head 30.

Other, alternative arrangements may be used. For example, FIG. 3 shows an alternative to the arrangement shown in FIG. 1 in which the sample containers B-1-B-5 are connected to a common node with a rotary valve 36 disposed at the node for selectively opening one of the sample containers connected to the node while the other sample containers remain closed.

The aseptic sample withdrawal system described herein includes the dual-filter design that allows the system to be selectively opened to atmosphere without jeopardizing the sterility of the closed system, thereby allowing the culture fluid trapped in the sampling line 24 to be pumped back into the vessel 20 or into one of the sample containers B-1-B-5 by alternating the flow direction within the sampling line 24 after the desired amount has been captured in the selected sample container. This eliminates the wasteful purge step, which can affect the final harvest volume, especially for smaller working volumes, as well as the unsanitary waste reservoir, where cells can die and lyse. The added advantage is that any bi-directional (e.g., peristaltic) pump can be used with this system, since there is no purge step and therefore no limitation in tubing size. The flexibility in tubing size used in the system also enables the user to choose from a wide variety of tube welding or aseptic connection options.

Figure 2:
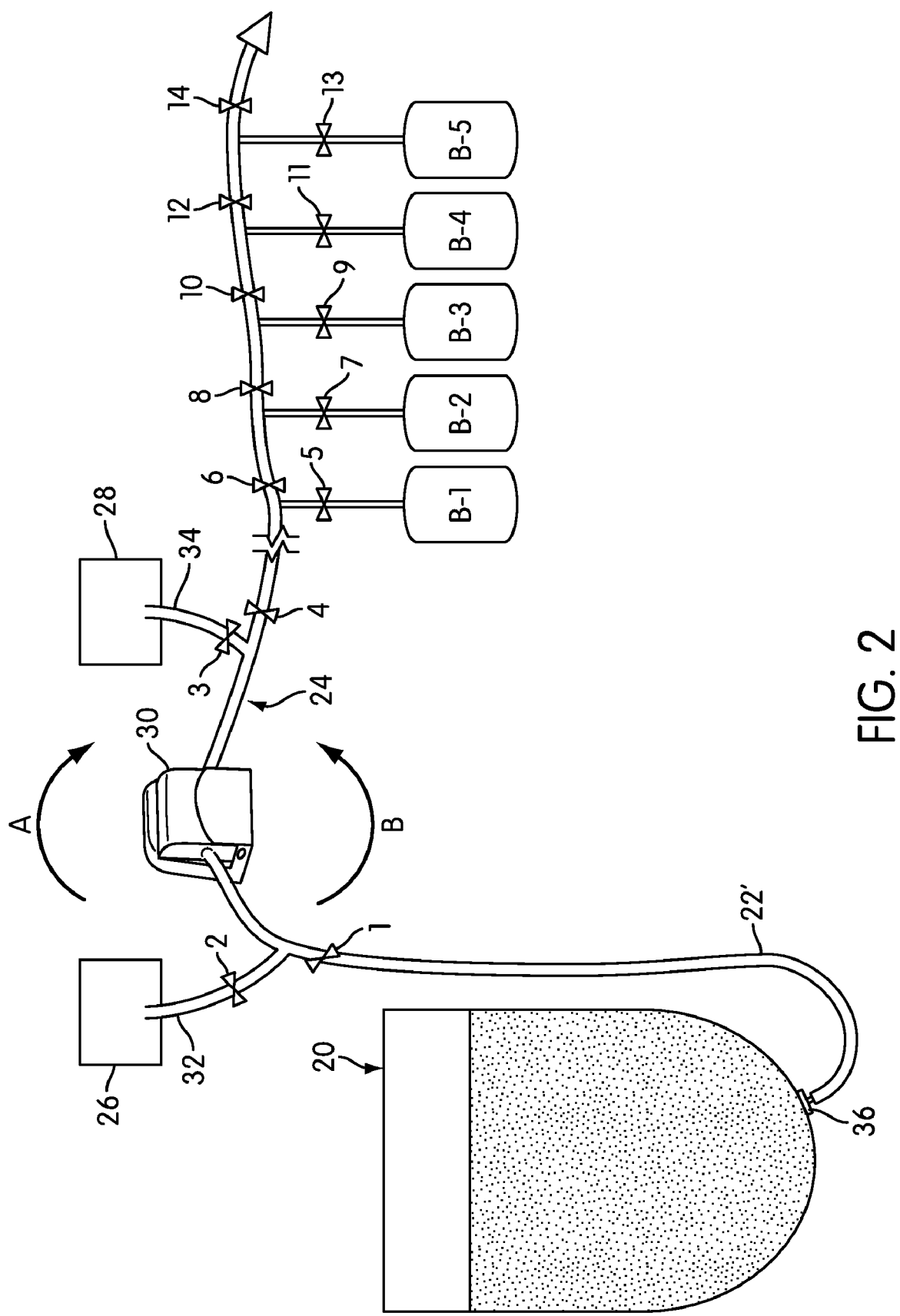
FIG. 2 is a schematic drawing of an alternative embodiment of an aseptic sample withdrawal system embodying aspects of the invention.
Figure 3:
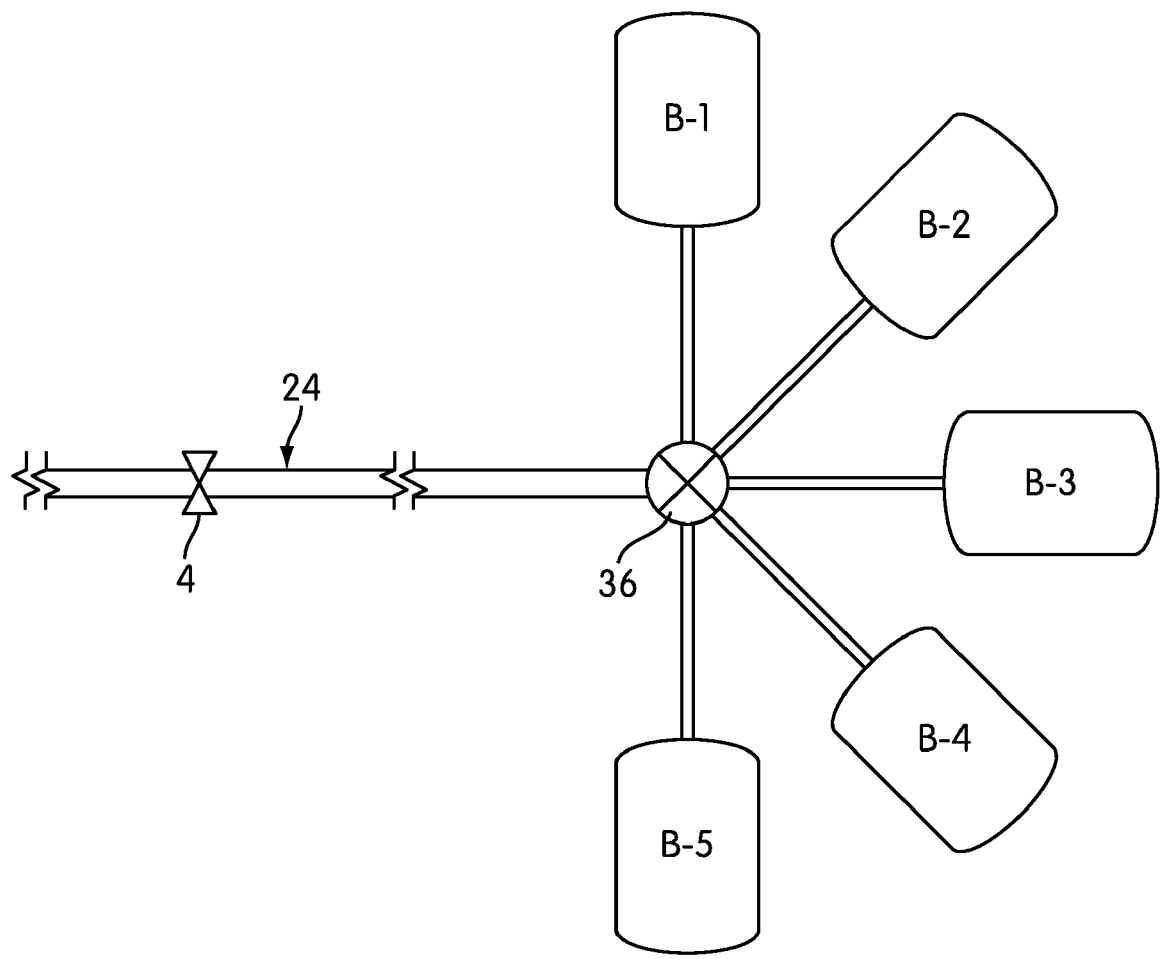
FIG. 3 is a schematic drawing of another alternative embodiment of an aseptic sample withdrawal system embodying aspects of the invention.

A sampling procedure for the system as shown in FIGS. 1-3, which can be automated by a computer controller or manipulated manually, is shown by flow chart 50 in FIG. 4 and described below. The procedure is described with respect to the sampling system shown in FIG. 1.

In step 52, the sampling line 24 is purged to ensure there is no residual fluid in the sampling line 24 by pumping residual fluid from the sampling line 24 back into the vessel 20. In the system of FIG. 1, step 52 is performed by: (a) closing sampling line 24 on the sampling side of the pump by closing valve 4, (b) venting the sample side of the sampling line 24 by opening valve 3 of the sample side vent line 34, (c) opening the sampling line 24 on the vessel side of the pump 30 by opening valve 1, (d) closing the sample side venting line 32 by closing valve 2, and then (e) operating pump 30 in direction B to pump any residual fluid contained in the sampling line 24 into the vessel 20. Steps (a) through (d) do not necessarily need to be performed in the order listed, but step (e), operating the pump, should not be performed until all the valves are opened or closed, as required. Although valve 4 closes off the sampling line to all of the sampling containers B-1 through B-5, valves 5-14, which are downstream of valve 4, may also be closed to redundantly close off the sample containers In step 54, a prescribed volume of sample material is withdrawn from the vessel 20 and is deposited in one of the sample containers B-1 through B-5. In the system of FIG. 1, step 54 is performed by: (a) opening the vessel side of the sampling line 24 by opening valve 1, (b) opening the sample side of the sampling line 24 by opening valve 4, (c) closing both vessel side vent line 32 and sample side vent line 34 by closing valves 2 and 3, respectively, (d) opening the first sample container B-1 by opening valve 5, (e) closing the remaining sample containers B-2 through B-5 by closing valve 6, and then (f) operating the pump 30 in the direction A for a prescribed period of time (or a prescribed number of revolutions) to transfer a prescribed volume of sample material from the vessel 20 into the container B-1. Steps (a) through (e) do not necessarily need to be performed in the order listed, but step (f), operating the pump, should not be performed until all the valves are opened or closed, as required.

In step 56, any residual sample fluid in the sampling line 24 is pumped back into the vessel 20. In the system of FIG. 1, step 56 is performed by: (a) closing off the sample side of the sampling line 24 by closing valve 4 and/or valve 5, (b) venting the sample side of the sampling line 24 by opening valve 3 of sample side vent line 34, (c) closing valve 2 of the vessel side vent line 32, (d) opening the vessel side of the sampling line 24 by opening valve 1, and (e) operating pump 30 in direction B to move fluid from the sampling line 24 back into the vessel 20 without removing any fluid from container B-1. Again, the order in which the steps are performed, other than operation of the pump, is not necessarily critical.

In step 58, any remaining residual fluid downstream of valve 4 and/or valve 5 is purged from the sampling line 24. In the system of FIG. 1, step 58 is performed by: (a) closing off the vessel side of the sampling line 24 by closing valve 1, (b) venting the vessel side of the sampling line 24 by opening valve 2 of vessel side vent line 32, (c) closing sample side vent 34 by closing valve 3, (d) opening the container B-1 by opening valves 4 and 5, (e) closing the remaining sample containers B-2 through B-5 by closing valve 6, and then (f) operating pump 30 in direction A to remove any remaining fluid from the sampling line 24 into the sample container B-1 without withdrawing any additional fluid from the vessel 20. Again, the order in which the steps are performed, other than operation of the pump, is not necessarily critical.

In step 60, the just-filled sample container B-1 is removed from the system. Step 60 is performed by closing the valve 5 and cutting or otherwise removing sample container B-1 from the system.

Steps 52 to 62 are repeated for each of the other sample containers to be filled. Implementation of the steps differs somewhat in that different valves must be operated to fill different sample containers. For example, to fill sample container B-2, valves 6 and 7 are opened while valves 5 and 8 remain closed. To fill sample vessel B-3, valves 6, 8, and 9 are opened while valves 5, 7, and 10 are closed. To fill sample container B-4, valves 6, 8, 10, and 11 are opened while valves 5, 7, 9, and 12 are closed. And to fill sample container B-5, valves 6, 8, 10, 12, and 13 are opened while valves 5, 7, 9, 11, and 14 are closed.

In an alternative procedure, the order of steps 56 and 58 can be reversed. That is, after performing step 54, step 58 can be performed with the system of FIG. 1 by: (a) closing off the vessel side of the sampling line 24 by closing valve 1 and (b) venting the vessel side of the sampling line 24 by opening valve 2 of vessel side vent line 32 while (d) continuing to operate pump 30 in direction A to pump remaining fluid from the sampling line 24 into the sample container B-1 without withdrawing any additional fluid from the vessel 20. After step 58, step 56 can be performed with the system of FIG. 1 by: (a) closing off the sample side of the sampling line 24 by closing valve 4 and/or valve 5, (b) venting the sample side of the sampling line 24 by opening valve 3 of sample side vent line 34, (c) closing valve 2 of the vessel side vent line 32, (d) opening the vessel side of the sampling line 24 by opening valve 1, and (e) operating pump 30 in direction B to move fluid from the sampling line 24 back into the vessel 20 without removing any fluid from container B-1.

Figure 5:
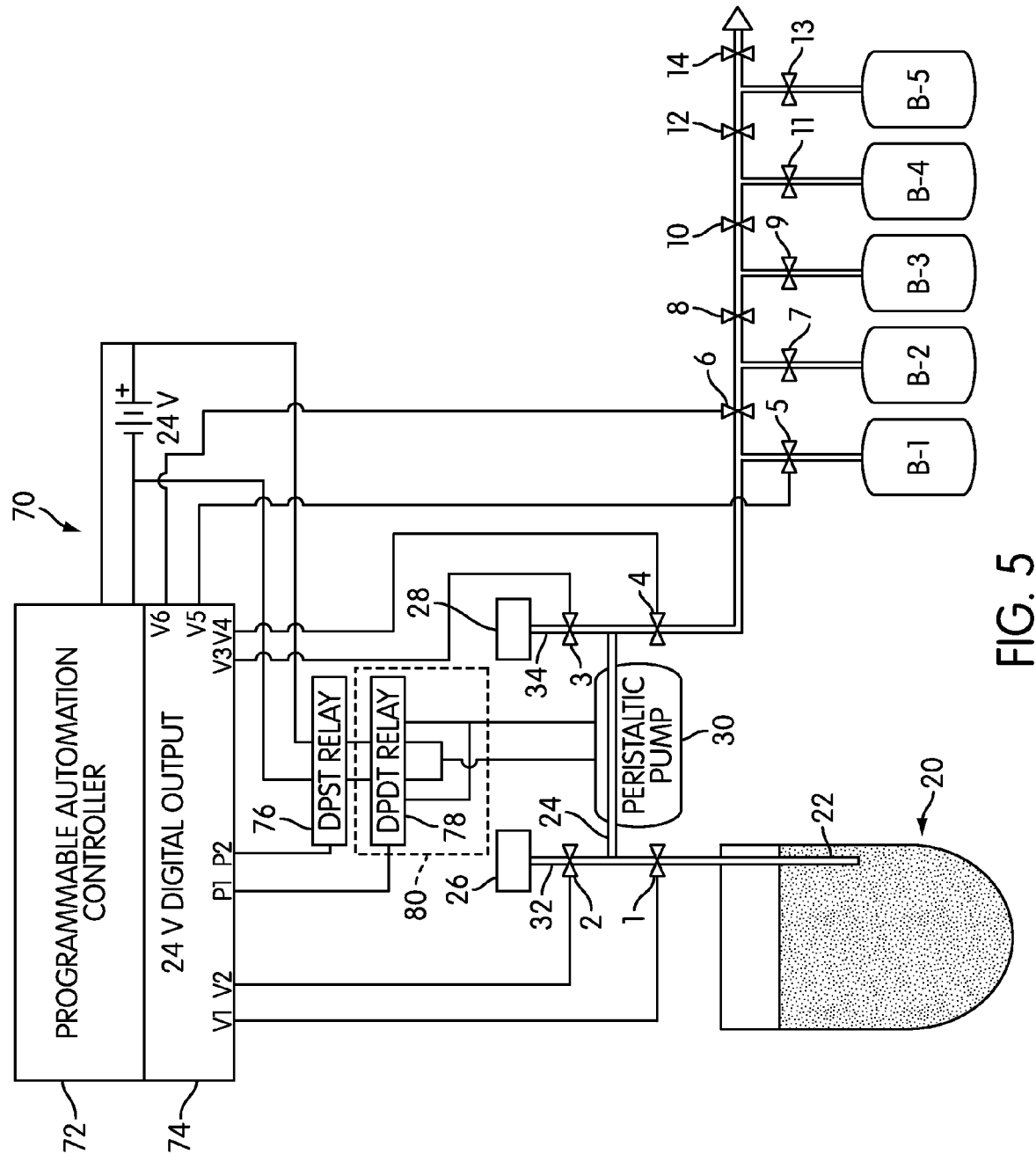
FIG. 5 is a schematic diagram of a control system for automation of the sample withdrawal system and sampling procedure.

FIG. 5 schematically shows the sampling system incorporated with an automated control system 70 configured to automatically control operation of the valves of the flow control system and the pump 30. The automated control system 70 includes a programmable automation controller ("PAC") 72. A suitable PAC is available from National Instruments Model No. sbRIO 9641. The PAC 72 includes a 24 volt digital output 74, which is connected to each of the valves 1-14 (the connection of digital output 74 to valves 7-14 is not shown in FIG. 5 so as to avoid obscuring the drawing). The pump 30 is connected to the digital output via a DPDT (double pole double throw) relay 78 and a DPST (double pole single throw) relay 76. In the illustrated embodiment, the PAC 72 and the relays 76, 78 are connected to a 24 volt power source.

Figure 4:
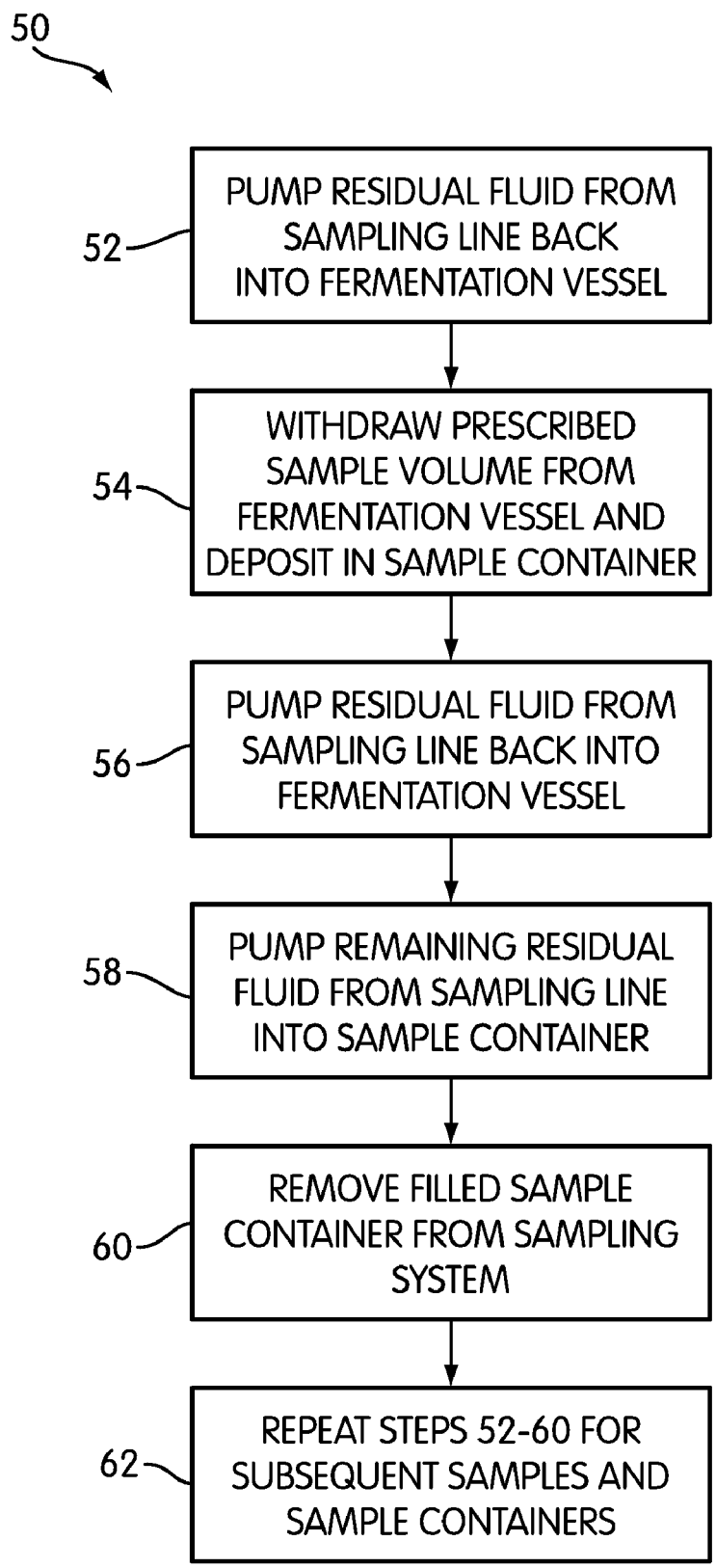
FIG. 4 is a flow chart showing steps performed in an aseptic sampling procedure embodying aspects of the invention.

The PAC 72 is programmed with a sequencing algorithm, such as an algorithm that will implement the process shown in FIG. 4. Initiation of the sampling sequence may be programmed into the PAC 72 so as to be automatic, or the sampling sequence may be initiated by a user via a user interface. In one embodiment, each of the valves 1-14 is an electronic pinch valve that is normally in a closed state and may be opened by a signal generated by the PAC 72 and output by the digital output 74. As shown in the illustrated embodiment, the PAC 72 and digital output 74 generate a dedicated signal V1, V2, V3, V4, V5, V6, etc., for each of the valves 1-14, respectively. The P2 output, along with the controls of the DPST relay 76, govern whether power gets to the DC motor of the pump 30. The P1 output, along with the controls of the DPDT relay 78, changes the polarity of the power that gets to the DC motor of the pump 30 thereby controlling the direction of the pump. In an embodiment of the invention, the PAC effects a timing-based control of the valves and the pump to transfer a desired volume fluid, in one direction or the other, based on the volume of the sampling lines and the flow rate of the pump.

Figure 6:
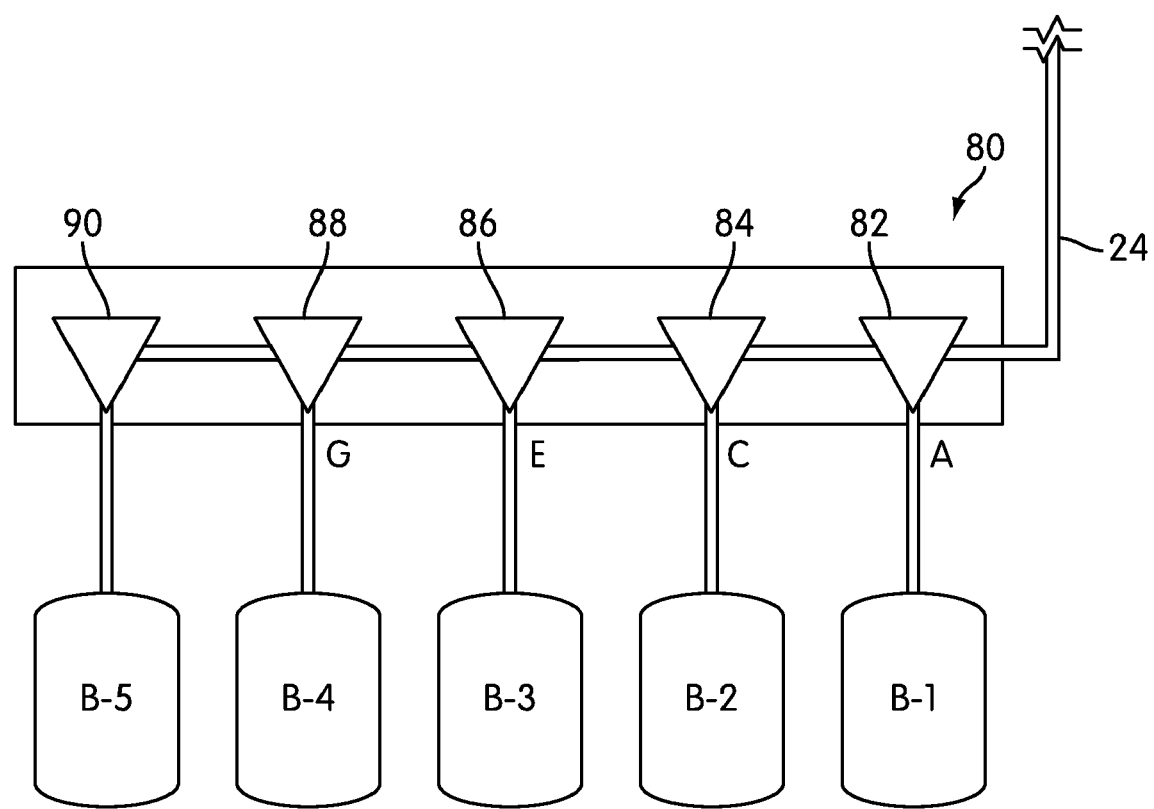
FIG. 6 is a schematic view of a sample manifold for selectively connecting individual sample containers to a main sampling line in accordance with an embodiment of the invention.

In an alternate embodiment, valves 5-14 of the flow control system are not connected to the PAC 72 and are not automatically controlled. In such an embodiment, the appropriate valves are open and closed manually. In still other embodiments, valves 5-14 are omitted from the flow control system altogether, and the appropriate flow control is achieved using clamps or hemostats at pinch points in the main and secondary sample tubing corresponding to the locations of valves 5-14 shown in FIGS. 1 and 2. In a still further embodiment, shown in FIG. 6, the flow control system includes a manifold 80 connected to the main sampling line 24, and each of the sample containers B-1, B-2, B-3, B-4, and B-5 is coupled to the sample manifold 80 via an associated three-way stopcock 82, 84, 86, 88, and 90. Reference characters A, C, E, and G indicate pinch points in the secondary sampling lines were clamps are placed when the associated sample containers are removed.

An exemplary sampling sequence using the automated system 70 is described below.

Before the sampling sequence commences, each of the automatically-controlled valves 1-4 is closed and the pump 30 is not operating. Digital output 74 outputs an "off" or null signal for outputs V1, V2, V3, V4, P1, and P2. Valves 5-6 are closed, either manually or via an "off" or null signal from the digital output 74 of the PAC, or main and secondary sampling lines are clamped at pinch points corresponding to the locations indicated by valves 5-14. The sampling sequence is initiated by a user at a user interface, or a prescheduled sampling sequence may be programmed into the PAC 72 for automatic initiation by the PAC 72. To perform the sampling sequence, generally corresponding to step 54 in FIG. 4, the PAC 72 opens valve 1 by changing signal V1 to "on" and opens valve 4 by changing signal V4 to "on" to open the sampling line 24. Valve 5 is opened, either automatically or manually, or the clamp is removed from the pinch point 5. Thus, the sampling lines are open from the vessel 20 to the first sample container B-1.

Signal P1 is changed to "on" and signal P2 is changed to "on" to operate the pump 30 in a forward direction to pump fluid from the vessel 20, through the main and secondary sampling lines, and into the sample container B-1. At a first prescribe time lapse (ΔT1) following the initiation of the sample pumping sequence, the sampling sequence is terminated, and a forward flush (corresponding to step 58 in FIG. 4) is performed. PAC 72 changes signal V1 to "off" to close valve 1, thereby terminating sample flow from the vessel 20, and changes signal V2 to "on" to open the valve 2 and vessel side vent line 32 to vent the vessel side of sampling line 24. Signals P1 and P2 remain "on" to continue forward flow of the pump 30, V3 remains "off" and V4 remains "on" to continue flow into the sample container B-1 without drawing additional fluid from the vessel 20 thereby clearing fluid from the sampling line 24. The length of the time lapse ΔT1 for beginning the flush sequence is calculated from the tubing volume in the system, the desired sample volume (which may be input by the user), and the pump flow rate.

At a second prescribed time lapse (ΔT2) following initiation of the sampling sequence a reverse flush (corresponding to step 56 in FIG. 4) is performed. PAC 72 changes signal V1 to "on" to open valve 1, thereby connecting vessel 20 to the sampling line 24, changes signal V2 to "off" to close valve 2, thereby closing sample side vent line 32, changes signal V3 to "on" to open valve 3 to open the valve 3 and sample side vent line 34 to vent the sample side of sampling line 24, changes signal V4 to "off" to close valve 4, thereby closing off the sample containers, and changes signal P1 to "off" while keeping signal P2 at "on" to cause a reverse flow of the pump 30 to pump any fluid remaining in sampling line 24 and dip tube 22 into the vessel 20 without pumping any fluid from the sample container B-1.

The sample sequence is terminated at a third prescribed time lapse (ΔT3) from initiation of the sampling sequence by turning all signals to "off", thereby closing valves 1-4 and stopping pump 30. The second and third time lapses, ΔT2 and ΔT3, are calculated from the tubing volume and the pump flow rate.

Sample container B-1 is then removed by closing valve 5, either manually or automatically, or by clamping the secondary sampling line at the pinch point corresponding to the location of valve 5, and then cutting the secondary sampling line below the valve or clamp. To take the next sample, valves 6 and 7 are opened, or the user opens the clamps at pinch points corresponding to the locations of valves 6 and 7, and valve 8 is closed, or the user clamps the tubing at a pinch point corresponding to the location of valve 8. The sampling sequence is repeated as described above, and, after sample container B-2 is filled and the sampling lines are flushed out, valve 7 is closed, or the secondary sample tubing is clamped at the pinch point corresponding to valve 7, and the secondary sampling line connecting container B-2 is cut below the valve or clamp.

A similar process is performed for each of the remaining sample containers B-3, B-4, and B-5.

Thus, exemplary embodiments have been fully described above with reference to the drawing figures. Although the invention has been described based upon these exemplary embodiments, it would be apparent to those of skill in the art that certain modifications, variations, and alternative constructions could be made to the described embodiments within the spirit and scope of the invention.

What is claimed is:

1. A system for withdrawing discrete fluid samples from a vessel adapted to contain a fluid;
   a main sampling line in fluid communication with the vessel;
   a pump in fluid communication with said main sampling line and adapted to selectively pump fluid from in the main sampling line in a first direction away from the vessel or a second direction toward the vessel;
   a first vent port in fluid communication with said main sampling line and disposed on a first side of said pump;
   a second vent port in fluid communication with said main sampling line and disposed on a second side of said pump;
   one or more sample containers in fluid communication with a portion of said main sampling line on the second side of said pump; and a flow control system adapted to be selectively configured to open or close each of said first and second vent ports, open or close one or more portions of said main sampling line, and open or close each sample container, wherein, in a first configuration of said flow control system, said first and second vent ports are closed, said main sampling line is open on the first and second sides of said pump, and at least one sample vessel is open, so that the pump can be operated in a first direction to move an amount of fluid from the vessel, through a portion of the main sampling line, and into the open sample container;

in a second configuration of said flow control system, said first vent port is closed, said second vent port is open, each of the one or more sample vessels is closed, and a portion of said main sampling line on the first side of said pump is open so that the pump can be operated in a second direction to move fluid disposed in said main sampling line into the vessel without withdrawing fluid from the at least one sample container; and in a third configuration of said flow control system, said first vent port is open, said second vent port is closed, said main sampling line is closed on the first side of said pump and opened on the second side of said pump, and the at least one sample container is open so that the pump can be operated in the first direction to move fluid disposed in the main sampling line and into the open sample container without withdrawing additional fluid from the vessel.

2. The system of claim 1, wherein said flow control system comprises:
 a first valve in said main sampling line between said vessel and said first vent port;
 a second valve in said first vent port;
 a third valve in said second vent port; and
 a fourth valve in said main sampling line between said second vent port and said sample containers.

3. The system of claim 2, wherein each of said valves is a pinch valve.

4. The system of claim 1, wherein said vessel comprises a fermentor, a bioreactor, or a medium batching holding vessel.

5. The system of claim 1, further comprising a filter associate with each of said first and second vent ports.

6. The system of claim 5, wherein each filter comprises a sterilizing grade gas filter with a 0.2 μm membrane.

7. The system of claim 1, wherein said pump comprises a peristaltic pump.

8. The system of claim 1, further comprising an automated control system adapted to:
 (a) automatically configure said flow control system in the first configuration,
 (b) automatically operate said pump in the first direction for a first prescribed period of time when said flow control system is in the first configuration,
 (c) automatically configure said flow control system in the second configuration,
 (d) automatically operate said pump in the second direction for a second prescribed period of time when said flow control system is in the second configuration,
 (e) automatically configure said flow control system in the third configuration, and
 (f) automatically operate said pump in the first direction for a third prescribed period of time when said flow control system is in the third configuration.

9. The system of claim 1, wherein each sample container is connected to a respective secondary sampling line branching from said main sampling line and said flow control system comprises a sample valve associated with each sample container and disposed in each secondary sampling line.

10. The system of claim 2, wherein each sample container is connected to said main sampling line by an associated secondary sampling line, and wherein said flow control system further includes a valve in each secondary sampling line and a valve in said main sampling line between each adjacent pair of secondary sampling lines.

11. The system of claim 2, wherein each sample container is connected to said main sampling line by an associated secondary sampling line, and wherein said flow control system further includes a clamp in each secondary sampling line that may be opened or closed to permit or prevent flow through the associated secondary sampling line and into the sample container.

12. The system of claim 2, wherein said flow control system further includes a rotary valve at which all of the sample containers are connected to the main sampling line and which is configured to selectively connect said main sampling line with one of said sample containers.

13. The system of claim 2, wherein said flow control system further includes a sample manifold connected to said main sampling line and to which each of said sample containers is connected, said sample manifold comprising a stop cock associated with each sample container connected to said manifold for selectively opening a fluid flow path from said main sampling line, through said manifold, and into said sample container.

14. A method for aseptically removing a sample portion of a fluid from a vessel containing the fluid comprising:
 A. providing a fluid flow connection between the vessel and a sample container;
 B. pumping fluid in a first direction from the vessel to the sample container through the fluid flow connection;
 C. disconnecting the vessel from the fluid flow connection, opening a vent upstream from the pump, and pumping fluid in the first direction through the fluid flow connection into the sample container without pumping any additional fluid from the vessel; and
 E. closing the upstream vent, reconnecting the vessel to the fluid flow connection, disconnecting the sample container from the fluid flow connection, opening a vent downstream from the pump, and pump fluid in a second direction opposite the first direction through the fluid flow connection and into the vessel without pumping any fluid from the sample container.

* * * * *